US005733780A

United States Patent [19]
Briggs et al.

[11] Patent Number: 5,733,780
[45] Date of Patent: Mar. 31, 1998

[54] **CONSTRUCTION OF *PASTEURELLA HAEMOLYTICA* VACCINES**

[75] Inventors: Robert E. Briggs, Boone; Fred M. Tatum, Ames, both of Iowa

[73] Assignees: The United States of America as represented by the Department of Agriculture, Washington, D.C.; Biotechnology and Research and Development Corporation, Peoria, Ill.

[21] Appl. No.: 643,298

[22] Filed: May 8, 1996

Related U.S. Application Data

[62] Division of Ser. No. 162,392, Dec. 6, 1993, Pat. No. 5,587,305.

[51] Int. Cl.$^6$ .................... C12N 15/74; C12N 15/00
[52] U.S. Cl. .................... 135/320.1; 435/172.3; 435/320.1
[58] Field of Search .................... 435/320.1, 172.3

[56] References Cited

U.S. PATENT DOCUMENTS

| | | | |
|---|---|---|---|
| 4,293,545 | 10/1981 | Kucera | 424/255.1 |
| 4,335,106 | 6/1982 | Kucera | 424/255.1 |
| 4,346,074 | 8/1982 | Gilmour et al. | 424/203.1 |
| 4,388,299 | 6/1983 | Kucera | 424/255.1 |
| 4,506,017 | 3/1985 | Kucera | 435/252.1 |
| 4,559,306 | 12/1985 | Kucera | 435/252.1 |
| 4,626,430 | 12/1986 | Kucera | 424/255.1 |
| 4,735,801 | 4/1988 | Stocker et al. | 424/235.1 |
| 4,837,151 | 6/1989 | Stocker et al. | 424/200.1 |
| 4,888,170 | 12/1989 | Curtiss | 424/200.1 |
| 4,957,739 | 9/1990 | Berget et al. | 424/190.1 |
| 4,999,191 | 3/1991 | Glisson et al. | 424/255.1 |
| 5,055,400 | 10/1991 | Lo et al. | 424/235.1 |
| 5,077,044 | 12/1991 | Stocker et al. | 424/235.1 |
| 5,165,924 | 11/1992 | Shewen et al. | 424/236.1 |
| 5,210,035 | 5/1993 | Stocker | 424/235.1 |

OTHER PUBLICATIONS

Rossmanith et al., Am. J. Vet. Res., vol. 52, no. 12, Dec. 1991, pp. 2016–2022.
Haghouor et la., J. Vet. Medicine Series B, 34 (7), 1987, 509–518.
Bills et al., Plasmid 30, 268–273 (1993).
Chang et al., "Pneumonic pasteurellosis: Examination of typable and untypable *Pasteurella haemolytica* strains for Leukotoxin Production, Plasmic Content, and Antimicrobial Susceptibility." Am. J. Vet. Res., 48(3):378–384 (1987).
Homchamps et al., "Molecular Analysis of the aroA Gene of *Pasteurella Multocida* and Vaccine Potential of a Constructed aroA Mutant." *Molecular Microbiology*. 6(23):3585–3593 (1992).
Briggs et al., "Isolation of a Cryptic Plasmic from *Pasteurella haemolytica* by Electroporation," Abstract, 72nd Annual Meeting of the Conference of Research Workers in Animal Disease, Nov. 11, 1991.

Livrelli et al., "Sequence and Molecular Characterization of the ROB–1 β–Lactamase Gene from *Pasteurella haemolytica*," Antimicrobial Agents and Chemotherapy. 35(2):242–251 (1991).
Rickets et al., "Leukotoxin and Pathogenicity of *Pasteurella haemolytica*: Studies with a Leukotoxin Non–Producing Mutant", Abstract, 3rd International Veterinary Symposium, PS 7.19, p. 92 (1993).
Frey, "Construction of a Broad Host Range Shuttle Vector for Gene Cloning and Expression in *Actinobacillus pleuropnesumoniae* and Other Pasteurellaceae." Re. Microbiol. 143:263–269 (1992).
Craig et al., "A Plasmic Which Can Be Transferred Between *Eschrichia coli* and *Pasteurella haemolytica* by Electroporation and Conjugation." J. Gen. Microbiology. 135:2885–2890 (1989).
Boyce et al., "Plasmid Profile Analysis of Bovine Isolates of *Pasteurella haemolytica*," Am. J. Vet. Res., 47(6):1204–1206 (1986).
Schwarz, et al., "Detection and Interspecies–Transformation of a β–Lactamase–Encoding Plasmid from *Pasteurella haemolytica*," Zbl. Bakt. Hyg. A, 270462–469 (1989).
Haghour et al., "Plasmids and Resistance to 9 Chemotherapeutic Agents of *Pasteurella multocida* and *Pasteurella haemolytica*," J. Vet. Med. B 34:509–518 (1987).
Azad et al., "Distinct Plasmic Profiles of *Pasteurella haemolytica* Serotypes and the Characterization and Amplification of *Escherichia coli* of Ampicillin–Resistance Plasmids Encoding ROB–1 β–lactamase." J. Gen. Microbiology. 138:1185–1196 (1992).
Hoiseth et al., "Aromatic–dependent *Salmonella typhimurium* are Non–Virulent and Effective as Live Vaccines," Nature, 291:238–239 (1981).
Smith et al., "Vaccination of Calves Against *Salmonella dublin* With Aromatic–Dependent *Salmonella typhimirium*," Am. J. Vet. Res., 45(9):1858 (1984).
Roberts et al., "Construction and Characterization in vivo of *Bordetella pertussis* aroA Mutants," Infection and Immunity 58(3):732–738 (1990).
Ivins et al., "Immunization against Anthrax With Aromatic Compound–Dependent (Aro) Mutants of *Bacillus anthracis* and with Recombinant Strains of *Bacillus subtilis* That Produce Anthrax Protective Antigen." Infection and Immunity, 58(2):303–308 (1990).
Robertsson et al., "*Salmonella typhimurium* Infection in Calves: Protection and Survival of Virulent Challenge Bacteria After Immunizataion with Live or Inactivated Vaccines," Infection and Immunity 41(2):742–750 (1983).

(List continued on next page.)

Primary Examiner—Nancy T. Vogel
Attorney, Agent, or Firm—Banner & Witcoff, Ltd.

[57] ABSTRACT

Methylation of DNA can be a critical step in the introduction of DNA into *P. haemolytica*. A methyltransferase has been isolated and molecularly cloned for this purpose. Use of the methyltransferase has allowed construction of defined, attenuated mutants for use as vaccines to protect cattle.

4 Claims, 7 Drawing Sheets

OTHER PUBLICATIONS

O'Gaora et al., "Cloning and Characterization of the serC and aroA Genes of *Yersinia enterocolitica*, and Construction of an aroA mutant," *Gene* 84:23–30 (1989).

Chang et al., "Characterization of Plasmids With Antimicrobial Resistant Genes in *Pasteurella haemolytica* A1," *J. DNA Sequencing and Mapping*, 389–97 (1992).

Rossmanith et al., "Characterization and Comparison of Antimicrobial Susceptibilities and Outer Membrane Protein and Plasmic DNA profiles of *Pasteurella haemolytica* and Certain Other Members of the Genus Pasteurella," *Am. J. Vet. Res.*, 52(12):2016–2022 (1991).

Tatum et al., "Isolation, Identification, and Cloning of a Non–Palindromic Type II DNA Restriction Endonuclease Pha I, From *Pasteurella haemolytica*", Abstract of presentation at American Society for Microbiology, Annual Meeting, May 1993.

Yang et al., J. Bact., 160(i); 15–21 (1984).

Matsushima et al., J Bact., 169(5):2298–2300 (1987).

Marmelstein et al., Appl. Environ. Micro. (59/4): 1077–1081 (1993).

Wilson, Gene 74: 281–289 (1988).

Marra et al., J. Bact., 171/4:2238–2240 (1989).

Briggs et al., "Characterization of a Restriction Endonuclease, PhaI from *Pasteurella haemolytica* Serotype A1 and Protection of Heterologous DNA by a Cloned PhaI Methyltransferase Gene", *Applied and Environmental Microbiology* 60(6):2006–2010 (1994).

Tatum et al., "Molecular Gene Cloning and Nucleotide Sequencing and Construction of an aroA Mutant of *Pasteurella haemolytica* Serotype A1", *Applied and Environmental Microbiology* 60(6):2011–2016 (1994).

Old, et al., "Principles of Gene Manipulation", Blackwell Scientific Publications, Oxford, 1989.

Lunnen et al., "Cloning Type–II Restriction and Modification Genes", *Gene* 74:25–32 (1988).

Homchampa et al., "Construction and Vaccine Potential of an AroA Mutant of *Pasteurella haemolytica*", *Veterinary Microbiology* 42:35–44 (1994).

FIG. 4A

```
         30                        60                        90
TATGAGGCATTACTGCGTGAAGGCGTGATTGTTCGCTCGATAGCAGGTTATGAATGCCGAATCATTTACGCATTAGTATGCCTTACCG
         120                       150                       180
CAAGAAAACGAGAGATTTTTACTGCCTTATTGAAAGTGTTAGCTTAAACAAGCGGTTACCTTTTATGAAAATTTACAAATTTAAAGAGA
         210                       240                       270
AAAATGGAAAAACTAACTTAACCCCGATTTCCCGAGTAGAACGGAGATCAATTTATTAGATAGTGATATTCGACATGCTCAATGCCTTA
          M  E  K  L  T  L  T  P  I  S  R  V  E  G  E  I  N  L  P  G  S  K  S  L  S  N  R  A  L
         300                       330                       360
TTATTAGCGCCTTAGCCACCGGTACGACTCAAGTGACCAATTTATTAGATAGTGATATTCGACATATGCTCAATGCTTAAAAGCG
          L  L  A  A  L  A  T  G  T  T  Q  V  T  N  L  L  D  S  D  D  I  R  H  M  L  N  A  L  K  A
         390                       420                       450
TTAGGCGTGAAATATGAGCTATCGGACGATAAACCGTCTGTGTACTTGAAGGATTGGTGAGCTTTAAGGTTCAAAACGGCTTATCA
          L  G  V  K  Y  E  L  S  D  D  K  T  V  C  V  L  E  G  I  G  G  A  E  K  V  Q  N  G  L  S
         480                       510                       540
CTGTTTCTCGGCAATGCAGGCCACGCCACTTGCAGCAGCATTGTGTTTAAAAGGTGAGGAAAATCCCAAATCATTCTTACC
          L  F  L  G  N  A  G  T  A  M  R  P  L  A  A  A  L  C  L  K  G  E  E  K  S  Q  I  I  L  T
         570                       600                       630
GGTGAACCAAGAATGAAGAACGCCCGATTAAACACTTAGTCGATGCTTACCGCCAAGTAGGGGCAGAGTACAGTATTTAGAAATGAA
          G  E  P  R  M  K  E  R  P  I  K  H  L  V  D  A  L  R  Q  V  G  A  E  V  Q  Y  L  E  N  E
         660                       690                       720
GGCTATCCACCGTTGGCAATTAGCAATAGCGTTTGCAGGGCGGAAAAGTGCAAATTGACGCTCGATTCCAGCCAATTTCTAACCGCA
          G  Y  P  P  L  A  I  S  N  S  V  C  R  G  G  K  V  Q  I  D  G  S  L  S  S  Q  F  L  T  A
         750                       780                       810
TTGCTGATGTCTGCCCCATTAGCCGAAGGCGATATGGAAATTGAGATTATCGGTGATCGATCAAAACTTATATTCATATTACCCTT
          L  L  M  S  A  P  L  A  E  G  D  M  E  I  E  I  I  G  D  L  V  S  K  P  Y  I  D  I  T  L
```

FIG. 4B

```
         840                        870                        900
TCGATGATGAACGATTTTGGTATTACGGTTGAAAATCGAGATTACAAAACCTTTTAGTTAAAGTAAACAAGGCTATGTGCTCCACAA
 S  M  M  N  D  F  G  I  T  V  E  N  R  D  Y  K  T  F  L  V  K  G  K  Q  G  Y  V  A  P  Q
         930                        960                        990
GGTAATTATTGGTGGAGGGAGATGCCTTCTGCCTCTTATTTCTTAGCCTCCGGTGCGATTAAGGCAGTAAGTAACGGGCATTGGT
 G  N  Y  L  V  E  G  D  A  S  S  A  S  Y  F  L  A  S  G  A  I  K  A  G  K  V  T  G  I  G
         1020                       1050                       1080
AAAAAATCGATCCAAGGCGACCTGTTTGCCGATGTGTTGGAAAAAATGGGGGCAAAAATCACTTGGGGAGAGGATTTTATTCAAGCC
 K  K  S  I  Q  G  D  R  L  F  A  D  V  L  E  K  M  G  A  K  I  T  W  G  E  D  F  I  Q  A
         1110                       1140                       1170
GAGCAATCCCCGCTAAAAGGCGTAGATATGGATATGAATCATATTCCTGATGCGGCAATGACGATTGCAACAACCGCTTTATTGCCGAA
 E  Q  S  P  L  K  G  V  D  M  D  M  N  H  I  P  D  A  A  M  T  I  A  T  T  A  L  F  A  E
         1200                       1230                       1260
GGAGAAACAGTTATCCGCAATATTTATAACTGGCGGTAAAGAAACCGACCGCCTTGACAGCAATGGCAACCGAATTGCGTAAAGTCGGG
 G  E  T  V  I  R  N  I  Y  N  W  R  V  K  E  T  D  R  L  T  A  M  A  T  E  L  R  K  V  G
         1290                       1320                       1350
GCAGAGGTAGAAGAAGGGGAAGATTTTATTCGGATTCAACCGCTTGCGTTAGAAAACTTCCAGCACGCTGAAATTGAAACC
 A  E  V  E  E  E  G  E  D  F  I  R  I  Q  P  L  A  L  E  N  F  Q  H  A  E  I  E  T
         1380                       1410                       1440
TATAACGATCACCGTATGGCAATGTGTTTTTCATTAATTGCGTTATCGAATACAGAAGTGACGATCTTAGATCCAAATTGTACCGCTAAA
 Y  N  D  H  R  M  A  M  C  F  S  L  I  A  L  S  N  T  E  V  T  I  L  D  P  N  C  T  A  K
         1470                       1500                       1530
ACGTTCCCGACTTACTTTAGGGACTTGGAAAAATTATCGGTCAGATAAAAGTAAAAAAGGATTCAGAAAACTGAATCCTTTTTACGTTTT
 T  F  P  T  Y  F  R  D  L  E  K  L  S  V  R  *

ATTGTGGCAGACTAAGCCCAACCGCT
```

5,733,780

1

CONSTRUCTION OF *PASTEURELLA HAEMOLYTICA* VACCINES

This application is a division of application Ser. No. 08/162,392, filed Dec. 6, 1993, U.S. Pat. No. 5,587,305.

TECHNICAL AREA OF THE INVENTION

The invention relates to the area of bacterial genetic engineering. In particular, it relates to the bacteria *Pasteurella haemolytica*.

BACKGROUND OF THE INVENTION

The microorganism *P. haemolytica* biotype A, serotype 1, is the principal causative agent of pneumonic pasteurellosis in cattle. If techniques could be developed for introducing exogenous DNA into *P. haemolytica*, it would be possible to produce site-specific mutations in this bacterium. Such mutants could provide "rationally" attenuated strains for use as live vaccines.

Attenuated auxotrophic mutants were first described by Bacon and Burrows in the early 1950's. They reported that attenuated auxotrophs of *Salmonella typhi* defective in the aromatic amino acid biosynthetic pathway were avirulent in mice. Subsequently, it has been demonstrated in widely diverse bacteria that disrupting the aromatic amino acid biosynthetic pathway produces attenuated organisms. For example, attenuated strains of the invasive bacteria *Salmonella typhi*, *Salmonella typhimurium*, *Shigella flexneri*, and *Yersina enterocolitica*, were generated by introducing mutations in their respective aroA genes. Also attenuation was produced in the non-invasive bacteria *Bordetella pertussis* and *Pasteurella multocida* through aroA inactivation. Strains which carry aroA mutations are unable to synthesize chorismic acid from which p-aminobenzoic acid, dihydrobenzoate, and aromatic amino acids are produced. It is likely that the absence of one or more of these compounds in vivo is responsible for the poor growth of aroA mutants in the hosts.

Live attenuated bacterial strains generally provide superior protection as compared to killed bacterial vaccines (bacterins). In general, live vaccines elicit a stronger cell mediated response in the host than do bacterins. The superior immunity provided by attenuated live organisms may be explained by their ability to induce expression of stress-proteins and, possibly, of certain toxins within the host. The immune response generated by live organisms would be directed against these abundant proteins and thereby provide better protection.

There is a long-felt and continuing need in the art for veterinary vaccines to protect cattle from *P. haemolytica* infection. There also is a need for techniques for introducing DNA into *P. haemolytica*.

SUMMARY OF THE INVENTION

It is an object of the invention, to provide methods for mutagenizing *P. haemolytica*.

It is another object of the invention to provide a *P. haemolytica* gene for production of an enzyme for use in preparing genetic material for introduction into *P. haemolytica*.

It is yet another object of the invention to provide an enzyme for use in preparing genetic material for introduction into *P. haemolytica*.

It is still another object of the invention to provide a plasmid for unstable introduction of genetic material into *P. haemolytica*.

2

It is an object of the invention to provide *P. haemolytica* mutant strains.

It is another object of the invention to provide live, attenuated vaccines against *P. haemolytica* infection.

It is another object of the invention to provide genetically engineered *P. haemolytica*.

These and other objects of the invention are provided by one or more of the embodiments described below. In one embodiment of the invention a method for site-directed mutagenesis of *P. haemolytica* is provided. The method comprises the steps of: isolating a DNA region from *P. haemolytica* in which region a mutation is desired; introducing a mutation into said DNA region to form a mutated DNA region; methylating said mutated DNA region with a methylating enzyme, to form methylated DNA, which methylated DNA is refractory to endonuclease cleavage at GATGC and GCATC sequences; introducing said methylated DNA into *P. haemolytica* to form transformants; and screening said transformants for those which have said mutation in said region on chromosomal DNA of said *P. haemolytica* cell.

In an alternative embodiment of the invention site-directed mutagenesis of *P. haemolytica* is accomplished by the steps of: isolating a DNA region from *P. haemolytica* in which region a mutation is desired; introducing a mutation into said DNA region to form a mutated DNA region; introducing said methylated DNA into a *P. haemolytica* cell which does not express a PhaI restriction endonuclease, to form transformants; and screening said transformants for those which have said mutation in said region on chromosomal DNA of said *P. haemolytica* cell.

In another embodiment of the invention an isolated and purified gene is provided. The gene encodes PhaI methyltransferase.

In still another embodiment of the invention another isolated and purified gene is provided. The gene encodes PhaI restriction endonuclease.

In yet another embodiment of the invention a preparation of PhaI methyltransferase is provided. The preparation is free from PhaI restriction endonuclease.

In still another embodiment of the invention a preparation of PhaI restriction endonuclease is provided. The preparation is free from PhaI methyltransferase.

In another embodiment of the invention a chimeric plasmid is provided which is suitable for unstable introduction of genetic material into *P. haemolytica.* The plasmid comprises a 4.2 kb *P. haemolytica* plasmid encoding a streptomycin resistance determinant deposited at the American Type Culture Collection as Accession No. ATCC 69499; and a plasmid which cannot replicate in *P. haemolytica.*

In an additional embodiment of the invention a *P. haemolytica* mutant is provided. The mutant is made by the process of the invention described in more detail below.

In another embodiment of the invention a *P. haemolytica* mutant is provided which does not express the PhaI restriction endonuclease.

In another embodiment of the invention a *P. haemolytica* aroA mutant is provided.

In still another embodiment of the invention a vaccine is provided. The vaccine comprises an attenuated, live, mutant of *P. haemolytica* which has an aroA mutation.

In yet another embodiment of the invention an isolated and purified *P. haemolytica* strain is provided. The strain has been genetically modified by the introduction of DNA.

These and other embodiments ,of the invention provide the art with the means to construct desirable mutants of the economically important and previously intractable pathogen *P. haemolytica*.

BRIEF DESCRIPTION OF THE DRAWINGS

FIGS. 4A and 4B. Nucleotide sequence and deduced amino acid sequence of *P. haemolytica* aroA.

FIG. 6A. Lanes: 1, *P. haemolytica* strain NADC-D60; 2, aroA mutant; 3, pPharoA$^-$Amp$^R$pD70 probed with *P. haemolytica* aroA. FIG. 6B. Lanes: 1, *P. haemolytica* strain NADC-D60; 2, aroA mutant; 3, pPharoA$^-$Amp$^R$pD70 probed with *P. haemolytica* Amp$^R$ fragment. FIG. 6C. Lanes: 1, *P. haemolytica* strain NADC-D70; 2, aroA mutant; 3, pPharoA$^-$Amp$^R$pD70 probed with *P. haemolytica* Amp$^R$ plasmid. FIG. 6D. 1, *P. haemolytica* strain NADC-D60; 2, aroA mutant; 3, pPharoA$^-$Amp$^R$pD70 probed with pBCSK. DNA was isolated from *P. haemolytica* strain NADC-D70 and run in Lane 1 of blot B to demonstrate that if plasmid DNA was present in the bacteria it would also be present in our DNA preparations.

DETAILED DESCRIPTION OF THE PREFERRED EMBODIMENTS

Figure 1:
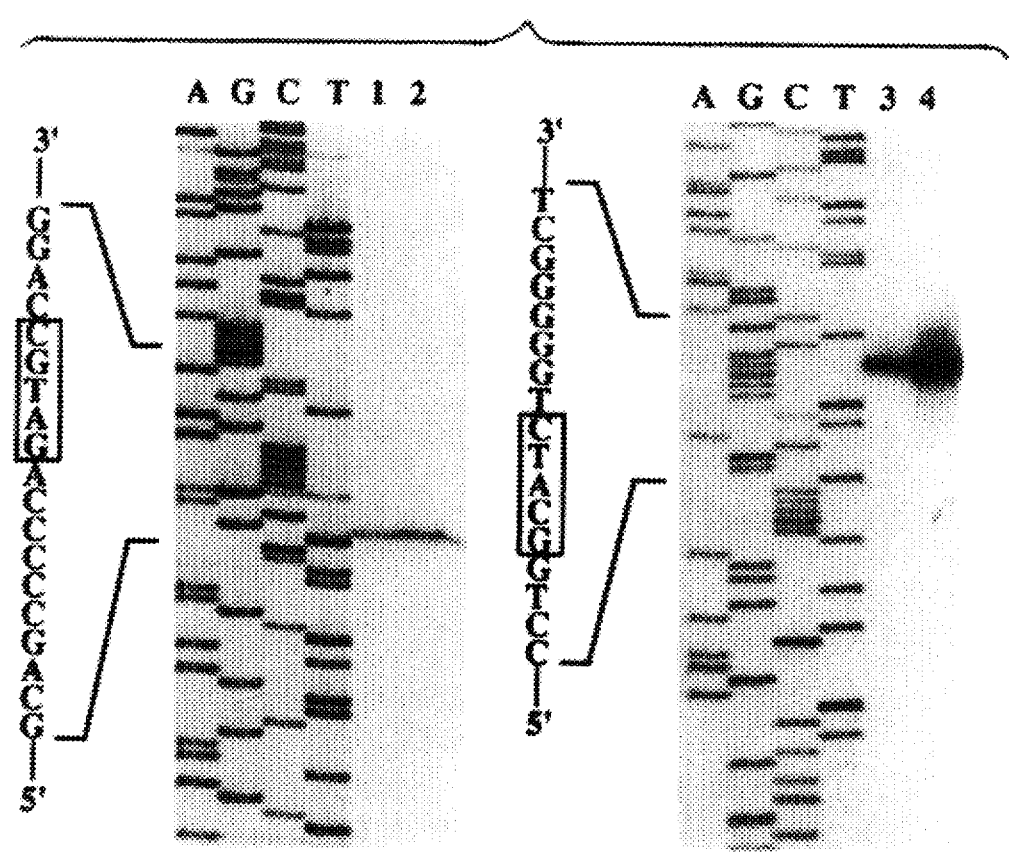
FIG. 1. Determination of PhaI cleavage positions alongside that of SfaNI. Lanes 1 and 3 cut with PhaI; lanes 2 and 4 cut with SfaNI. The cleavage products of PhaI and SfaNI migrated 0.5 bp faster than the corresponding sequence bands because the labeled primer for extension had a 5' phosphate, whereas the primer for sequencing did not (Juarin et al., *Gene* 39:191–201 (1985)).

It is a discovery of the present invention that *P. haemolytica* contains at least one restriction-modification system, called herein the PhaI system. Both the restriction endonuclease and the methyltransferase have been molecularly cloned. One such molecular clone (*E. coli* PhaIMtase) has been deposited at the American Type Culture Collection, 12301 Parklawn Drive, Rockville, Md., 20852, U.S.A., on Dec. 2, 1993, under the terms of the Budapest Treaty as Accession No. ATCC 69500. A preliminary sequence of the methyltransferase gene has been determined. The predicted amino acid sequence of the methyltransferase contains sequence motifs which are consistent with an adenine-methylating specificity.

Provided with the molecular clone of PhaIMtase (Accession No. ATCC 69500) one of ordinary skill in the art can readily obtain a preparation of either or both enzymes free of other *P. haemolytica* proteins. A lysate of a non-*P. haemolytica* bacterium carrying one of the cloned enzymes would provide such a preparation. If one desires a preparation of each of the enzymes free of the other enzyme, one of skill in the art can readily subclone to separate the two genes. The methyltransferase gene has been cloned into a plasmid which when introduced into a cell produces PhaI methyltransferase but is free of the PhaI restriction endonuclease. The PhaI restriction endonuclease gene can be cloned on a plasmid free of the methyltransferase gene by introduction of the cloned gene into host cells which express either the PhaI or the SfaNI methyltransferase.

Provided with PhaIMtase (ATCC Accession No. ATCC 69500) one of skill in the art can also readily obtain an isolated and purified gene encoding either or both the PhaI restriction and methyltransferase enzymes. Standard techniques, such as cesium chloride gradients, phenol and chloroform extractions, etc., can be used for purifying plasmid DNA from the deposited *E. coli* bacteria. The genes can be isolated together from the deposited bacteria, or they can be subcloned, as discussed above, to isolate the two genes from each other.

It has also been discovered by the present inventors, that a barrier to transformation of *P. haemolytica* can be overcome by treating DNA with a methylating enzyme, such as the PhaI methyltransferase. Such enzymes modify DNA substrates such that endonucleases which recognize 5'-GATGC-3' or 5'-GCATC-3' sequences are inhibited in their ability to digest such modified substrates. Examples of such endonucleases are PhaI endonuclease and SfaNI endonuclease. While applicants do not wish to be bound by any particular hypothesis on the mechanism of action of such methyltransferase enzymes, it appears that the PhaI methyltransferase methylates specific adenine residues in DNA.

Methylation of DNA substrates for transformation (electroporation, or other means of introduction of DNA into cells) can be accomplished in vitro or in vivo. For in vitro methylation, DNA is incubated with a preparation of methyltransferase in the presence of a methyl donor, such as S-adenosylmethionine (SAM). In vivo methylation can be accomplished by passaging the DNA substrate through a bacterium which contains an appropriate methyltransferase, such as PhaI or SfaNI methyltransferase. A mutant or natural variant of *P. haemolytica* which lacks the PhaI endonuclease could also be used to prepare DNA for subsequent introduction into *P. haemolytica*. Such a mutant can be made inter alia according to the method for site-directed mutagenesis disclosed herein.

Site-directed mutagenesis of *P. haemolytica* can be accomplished according to the present invention by first isolating a wild-type DNA region from *P. haemolytica*. As described below in the examples, an aroA gene can be isolated using aroA DNA from other bacteria as hybridization probes. The sequence of the *P. haemolytica* aroA gene is shown in SEQ ID NO. 1. Similarly other genes can be isolated from *P. haemolytica*. Another desirable gene for mutations is the PhaI endonuclease gene, which is provided in PhaIMtase (ATCC Accession No. ATCC 69500). Other genes in which mutations may be desirable are genes in the leukotoxin operon (C, A, B, D) and neuraminidase. A mutation is created in the isolated, wild-type DNA region according to any method known in the art. For example, the isolated DNA can be chemically mutagenized, either in a bacterium or in vitro. Alternatively, restriction endonucleases can be used to create precise deletions or insertions in vitro. Other methods as are known in the art can be used as is desirable for a particular application.

After *P. haemolytica* DNA has been isolated and mutagenized, it is methylated as described above. Then it can be introduced into *P. haemolytica* according to any technique known in the art, including but not limited to transfection, transformation, electroporation, and conjugation. Alternatively, rather than methylating the mutagenized DNA and introducing it into a *P. haemolytica* which expresses PhaI restriction endonuclease, one can omit the methylation of the mutagenized DNA and introduce the mutagenized DNA into a *P. haemolytica* cell which does not express the PhaI restriction endonuclease. Such cells can be isolated from nature by extensive screening, isolated following chemical mutagenesis of a cell which does express the PhaI restriction endonuclease, or made by the site-directed mutagenesis method disclosed herein.

According to one aspect of the invention, the mutagenized and methylated *P. haemolytica* DNA region is introduced into a *P. haemolytica* cell on a plasmid which includes a *P. haemolytica* approximately 4.2 kb streptomycin resistance determining plasmid (pD70). This plasmid has also been deposited at the American Type Culture Collection, 12301 Parklawn Drive, Rockville, Md., 20852, U.S.A., on Dec. 2, 1993, under the terms of the Budapest Treaty as Accession No. ATCC 69499. While applicants do not wish to be bound by any particular theory, it appears that the pD70 streptomycin resistance determining plasmid allows the introduced DNA to be replicated and maintained, albeit unstably, for a period of time sufficient to allow gene conversion (replacement of the chromosomal copy of the gene with the introduced mutant copy of the gene) to occur. Gene conversion can be monitored inter alia by Southern hybridization with probes to the gene of interest, by screening for genetic markers on the introduced DNA construct (such as ampicillin$^R$ or streptomycin$^R$), and by screening for the presence/absence of plasmid in the transformed cells' progeny.

A chimeric plasmid, as described above, is provided which is suitable for the unstable introduction of DNA into *P. haemolytica*. The chimeric plasmid comprises the approximately 4.2 kb streptomycin resistance determining plasmid, pD70, as well as a plasmid which cannot replicate in *P. haemolytica* but can replicate in another cell type. To use such a chimeric plasmid, typically a region of the chromosome of *P. haemolytica* which has been mutagenized is ligated into the plasmid. Maintenance of the chimeric plasmid in *P. haemolytica* can be selected, for example by using an appropriate antibiotic to which the plasmid confers resistance. After a selected number of generations, antibiotic selection can be removed, and the cells tested to determine whether the introduced region of *P. haemolytica* has replaced the genomic copy.

Also provided by the present invention are mutant strains made by the disclosed method of site-directed mutagenesis. One such mutant (NADC-D60 aroA$^-$) has been deposited at the American Type Culture Collection, 12301 Parklawn Drive, Rockville, Md., 20852, U.S.A., on Dec. 2, 1993, under the terms of the Budapest Treaty as Accession No. ATCC 55518. Such mutants can provide the veterinary arts with attenuated, live strains of *P. haemolytica* which are suitable for vaccines to induce protective immunity against *P. haemolytica* infection. For vaccine production, it is desirable that the mutation which attenuates the *P. haemolytica* be an essentially non-reverting mutation. Typically these are deletion or insertion mutations, the latter not being caused by a transposable element. Strains which contain multiple attenuating mutations may also be used, so that the risk of reversion to a wild-type, virulent *P. haemolytica* is vanishingly small.

Another mutant strain which can be made by the site-directed mutagenesis method disclosed is one which is PhaI restriction endonuclease negative. Such a strain is useful for genetic engineering in *P. haemolytica*. Such a strain can be a recipient of DNA which is not PhaI methyltransferase methylated, yet would yield DNA which is PhaI methyltransferase methylated.

The present invention thus allows those of ordinary skill in the art to stably introduce DNA into *P. haemolytica*. The DNA can be from other strains or species. The DNA can be artificially modified or in its native state. If recombination into the genome is desired two regions of flanking homology are preferred. Such techniques are generally known for other bacteria, but have been hitherto unsuccessful in *P. haemolytica* due to its restriction system.

Vaccines are typically formulated using a sterile buffered salt solution. Sucrose and/or gelatin may be used as stabilizers, as is known in the art. It is desirable that the *P. haemolytica* vaccines of the invention be administered by the intranasal or intratracheal route, but subcutaneous, intramuscular, intravenous injections also may be used. Suitable formulations and techniques are taught by Kucera U.S. Pat. No. 4,335,106, Gilmour U.S. Pat. No. 4,346,074, and Berget U.S. Pat. No. 4,957,739. Typically, between $10^7$ and $10^{11}$ CFU are administered per dose, although from $10^5$ to $10^3$ CFU can be used. Adjuvants also may be added.

EXAMPLES

Example 1

This example demonstrates the isolation and characterization of the type IIs restriction endonuclease PhaI.

Bacterium, growth, and crude extract

*Pasteurella haemolytica* serotype 1, strain NADC-D60, was grown 16 hours on 4 Columbia blood agar base plates (100 ml total volume, Difco, Detroit, Mich.) without supplemental blood. The cells were harvested in TE (10 mM Tris, 1 mM EDTA, pH 8.0), pelleted by centrifugation at 16,000 G for 5 minutes at 4° C., and washed once in TE. The washed pellet was resuspended in 1.5 ml chromatography running buffer (20 mM NaPO$_4$, 10 mM 2-mercaptoethanol, pH 7.5, 4 C) and placed on ice. The bacterial cells were disrupted by sonication for 2 minutes in 15 second bursts. Debris and unbroken cells were removed by centrifugation at 16,000 G for 10 minutes and then filtration of supernatant through a 0.45 um HA membrane. No further treatment of the crude extract was performed prior to chromatography.

Chromatographic separation of proteins

All chromatographic procedures were performed at room temperature. Prepacked heparin-sepharose columns [Econopac heparin columns, Bio-Rad, Richmond, Calif.] were equilibrated as recommended by the manufacturer. A flow rate of 0.5 ml/minute was used for separation, controlled by 2 HPLC pumps and a controller [Beckman Instruments, Inc, Fullerton, Calif.]. One ml of crude extract was injected and 10 ml of running buffer was used to wash the column. A linear gradient from 0 to 0.5M NaCl in 60 ml of running buffer was used to elute proteins. The column was washed with 2M NaCl in running buffer at 2.0 ml/minute as recommended by the manufacturer, then re-equilibrated to initial conditions of 0M NaCl in running buffer prior to additional runs. Fractions (1.0 ml) were stored on ice prior to activity assay, then frozen at −20° C.

Assay for restriction endonuclease activity

Aliquots, 5 μl, of the chromatographic fractions were incubated with 1 μl 12 mM MgCl and 0.25 μg unmethylated bacteriophage lambda DNA (New England Biolabs) at 37°

C. for 2 hours. After addition of tracking dye, and electrophoresis on a 1% agarose gel in TBE buffer, the banding patterns were visualized by ethidium bromide staining and UV illumination. The active fractions (6 ml) were pooled, concentrated 10-fold on 30,000 MW cutoff ultrafilters, and brought to final concentrations of 150 mM NaCl, 10 mM NaPO$_4$, 0.1 mM EDTA, 5 mM 2-mercaptoethanol, 0.25 µg/ml BSA, and 50:50 vol:vol glycerol [pH 7.5] for storage at −20° C.

Determination of the recognition sites for Pha I

The recognition sequence was identified using digestion of pBluescript (Stratagene, Lalolla, Calif.), which resulted in 4 fragments of approximate size 1476, 1057, 252, and 184 base pairs. Double digestion with PhaI and either XhoI or SacI, which cut at opposite ends of the polylinker, showed that one PhaI site mapped at approximately nucleotide 1245, and another at 2735. Additional double digestions with AvaII, BglII, DraII, PvuI and ScaI were used to map the remaining 2 PhaI sites at approximately nucleotides 2300 and 2490, consistent with the sequences 5'-GATGC-3' and 5'GCATC-3'. Further confirmation was made with PhaI digests of ΦX174 and pUC19 DNA, and by sequencing pBluescript PhaI fragments filled in and cloned into pBluescript. Single-stranded ΦX174 DNA was digested to determine if PhaI has activity on this substrate.

Determination of the cleavage sites for Pha I

The cleavage site was identified by digestion of a primed-synthesis reaction on pBluescript derivatives (Brown et at. (1980) J. Mol. Biol. 140:143–148). An oligonucleotide containing the PhaI site was annealed and ligated with Sma I-cleaved pBluescript SK+ and SK-DNA. Single-stranded DNA containing each orientation was selected and used for the template. Four standard dideoxy DNA sequencing reactions were performed for each template with an appropriate primer. Additional reactions containing no dideoxy terminator were extended through the PhaI site with the Klenow fragment of DNA polymerase I using $^{32}$P-endlabelled primer with both templates. The extension reaction was stopped by chloroform extraction followed by ethanol precipitation. PhaI or Sfa NI endonuclease was added to the additional reactions and allowed to digest the DNA for 2 minutes. The reaction was stopped by addition of gel loading buffer and heating to 80° C. for 3 minutes.

A new restriction endonuclease, PhaI, an isochizomer of SfaNI (Roberts (1990) Nucl. Acids Res. 18 (Suppl.), 2331–2365), was isolated from Pasteurella haemolytica serotype 1, strain NADC-D60, obtained from pneumonic bovine lung. PhaI recognizes the 5 base non-palindromic sequence 5'-GCATC-3' and 5'-GATGC-3'. Cleavage occurs five bases 3' from the former recognition site and nine bases 5' from the latter recognition site.

Under our experimental conditions, endonuclease activity was eluted from heparin-sepharose columns by 275 to 325 mM NaCl. A single pass through these columns was sufficient to allow identification of both the DNA recognition specificity and cleavage site. Approximately 5000 units of PhaI per gram of wet cells were recovered. In contrast to SfaNI, optimal conditions for PhaI digestion required NaCl or KCl concentrations below 50 mM; >50% reduction in activity was observed at the 100 mM NaCl optimum of SfaINI.

Digests of pBluescript resulted in 4 fragments of approximate size 1476, 1057, 252 and 184 bp. Double digestion with PhaI and either XhoI or SacI mapped 2 PhaI sites, one at approximately nucleotide 1245, and another at 2735 of pBluescript. Additional double digestions with PhaI and each of AvaII, BglII, DraI, PvuI, or ScaI mapped the remaining 2 PhaI sites at approximately nucleotides 2300 and 2490, consistent with the sequences 5'-GATGC-3' and 5'-GCATC-3'. Digests of pUC19, and ΦX174 confirmed the recognition specificity of 5'-GCATC-3', which is the same as that of SfaNI. Double digests of pBluescript with PhaI and SfaNI resulted in patterns identical to those using either enzyme alone. DNA containing the recognition sequence 5'-GATGC-3' cut 9 nucleotides 5' to the end of the recognition site with both PhaI and SfaNI. (FIG. 1, lanes 1 and 2) DNA containing the recognition sequence 5'-GCATC-3' cut 5 nucleotides 3' to the end of the recognition site with both PhaI and SfaNI. (FIG. 1, lanes 3 and 4)

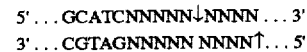

These data confirm that PhaI is a true isoschizomer of SfaNI. PhaI like SfaNI is a type IIs enzyme (Roberts, Nucleic Acids Res. 18:2331–2365 (1990)). The type IIs restriction enzymes, like the more common type II restriction enzymes, recognize specific sequences and cleave at predetermined sites. Type IIs enzymes, however, neither recognize palindromic sequences nor cleave internally to the recognition sequence (Szybalski, Gene 100:13–26 (1991)).

Example 2

This example demonstrates the molecular cloning of PhaI endonuclease and methyltransferase.

Cosmid Library Construction

High-molecular weight DNA for cosmid cloning was prepared by the large scale DNA isolation method described for gram-negative bacteria in Ausabel et al. (Current Protocols in Molecular Biology, Green Publishing Associates and Wiley Interscience, NY, N.Y. (1987)). Approximately 100 µg of P. haemolytica strain NADC-D60 genomic DNA was digested with 100U of ApoI in NEB buffer #3 at 50° C. for 10 minutes. Following digestion, the DNA was phenol-chloroform extracted and ethanol precipitated. The DNA was resuspended in 100 µl TE and layered onto a linear gradient of 10–40% sucrose (Schwartz-Mann Ultrapure) in 10 mM Tris HCl, 1 mM EDTA, 100 mM NaCl, pH 8.0. After centrifugation in a SW40 (Beckman Inst.) at 20,000 RPM for 20 hr, gradient fractions were collected and restriction fragments of approximately 30 kb in length were ligated into Eco RI-digested Calf alkaline phosphatase-treated cosmid vector pLAFRX (Ausabel, supra). A standard ligation mixture contained 1 µg vector, 3 µg P. haemolytica DNA and 5 Weiss U of T4 ligase in a volume of 10 µl. The ligation mixture was incubated at 10° C. for 16 hr. The DNA was packaged using Promega packaging extract (Promega, Madison, Wis.) according to the manufacturers' recommendations. E. coli HB101 transduced with the recombinant cosmid library were plated on 2XYT plates containing 10 µg/ml tetracycline. Cloning efficiencies were approximately 10$^4$ recombinant colonies per µg of genomic DNA.

Cloning of PhaI endonuclease and methyltransferase gene

Approximately 1 µg of the recombinant P. haemolytica cosmid library was digested with PhaI restriction enzyme. The digested DNA was phenol-chloroform:isoamyl alcohol-extracted, ethanol precipitated, and resuspended in TE buffer. The DNA was electroporated into E. coli AP1-200-9 (Piekarowicz et al., Nucl. Acids Res. 19:1831–1835 (1991)) and the cells were plated on LB-broth plates containing 20 µg/ml tetracycline and 35 µg/ml XgaI. The transformed cells were incubated at 42° C. for 18 hours and transferred to 30°

C. for 4 hours. The cells were moved again to 42° C. and blue colonies, indicating the presence of a cloned methyltransferase gene, were isolated and analyzed. The colonies were screened for restriction endonuclease activity by the technique of Schleif (*Method in Enzyraology*, vol. 65, part I, pp. 19–23 (1980)). Double-stranded DNA mini-preps isolated from restriction endonuclease-positive colonies were analyzed for resistance to digestion by PhaI. Recombinant colonies resistant to PhaI digestion were presumed to contain a PhaI methyltransferase gene. Cosmid DNA from these cells was electroporated into *E. coli* DH10B (BRL, Gaithersburg, Md.) and the cells were plated on LB-broth plates containing 20 μg/ml tetracycline. The transformants containing the PhaI methyltransferase gene were designated *E. coli* strain PhaIMtase.

After digestion with PhaI and transformation of AP1-200-9 strain of *E. coli*, fifteen cosmid clones of *P. haemolytica* genomic DNA were tested for endonuclease activity. The nine clones which were endonuclease-positive were tested for PhaI methyltransferase activity. All nine expressed methyltransferase activity in addition to endonuclease activity, as evidenced by resistance to digestion by PhaI of genomic DNA recovered from transformed *E. coli*. The selective recovery of clones containing functional methyltransferase was due to previous digestion of the cosmid library with PhaI prior to transformation of *E. coli*. Recovery of clones containing both PhaI endonuclease and methyltransferase activity is not surprising since restriction and modification enzymes have previously been shown to be closely linked (the proximity of such genes has obvious implications to gene inheritance and the survival of the organism). The AP1-200-9 strain of *E. coli* (used to screen the cosmid library in this experiment) was designed by Piekarowicz et at., to give color selection for DNA-modifying enzymes (genes). The mrr and mcr systems, with a temperature-sensitive phenotype, induce inducible locus of the SOS response allows for color selection. All the transformants were blue after incubation at the permissive temperature for the mcr/mrr systems. Recovery of clones containing both PhaI endonuclease and methyltransferase activity is not surprising since restriction and modification enzymes have previously been shown to be closely linked (the proximity of such genes has obvious implications to gene inheritance and to the survival of the organism). (Wilson et al., *Annu. Rev. Genet.* 25:585–627 (1991).)

Example 3

This example demonstrates the construction and methylation of a hybrid shuttle vector for introduction of DNA to *P. haemolytica*.

The following hybrid DNA construct was generated during attempts to introduce site-directed mutations into *P. haemolytica*. The aroA gene of *P. haemolytica*, contained on a HindIII-AccI fragment of genomic DNA from strain NADC-D60, was ligated into the HindIII-AccI site of pBluescript. A 700 bp fragment was excised from the coding region of the aroA gene by double digestion with NdeI and StyI. Following digestion, the fragment ends were made blunt by treatment with the Klenow fragment of *E. coli* polymeraseI and deoxynucleoside triphosphates. The deleted plasmid was excised from a 1% agarose gel and electroeluted. The eluted DNA, designated pPhΔaroA2, was phenol-chloroform extracted and ethanol precipitated. The fragment was resuspended in TE buffer and ligated with the $Cm^R$ gene isolated from pBR325. The $Cm^R$ gene was excised from pBR325 by double digestion with Aat II and ClaI and the fragment was made blunt and purified by the above methods. The $Cm^R$ fragment ligated with pPhΔaroA2 was given the designation pPhΔaroACm$^R$. Transformation of *E. coli* DH10B with pPhΔaroACm$^R$ conferred $Cm^R$ to the bacterium.

The hybrid plasmid pPhΔaroACm$^R$pD80 was constructed by ligating SmaI digested pPhΔaroACm$^R$ with ScaI digested pD80 (4.2 kb amp$^R$ plasmid from *P. haemolytica* serotype 1 strain NADC-D80). The resultant hybrid plasmid, approximately 11 kb in size, contained a ColE1 and *P. haemolytica* ori, amp$^R$, and $Cm^R$.

Figure 2:
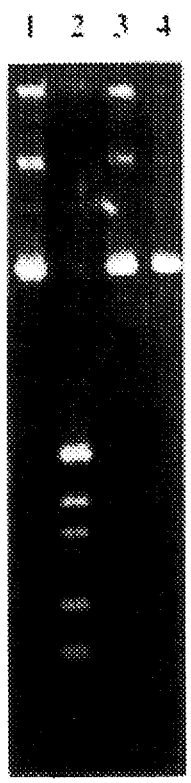
FIG. 2. Protection against PhaI digestion by cloned PhaI-methyltransferase. Lanes 1 and 2 plasmid pPhΔroACm$^R$-pD80 from *E. coli* DH10B incubated without and with PhaI. Lanes 3 and 4 plasmid pPhΔAroACm$^R$-pD80 from *E. coli* PhaIMtase incubated without and with PhaI.
Figure 3:
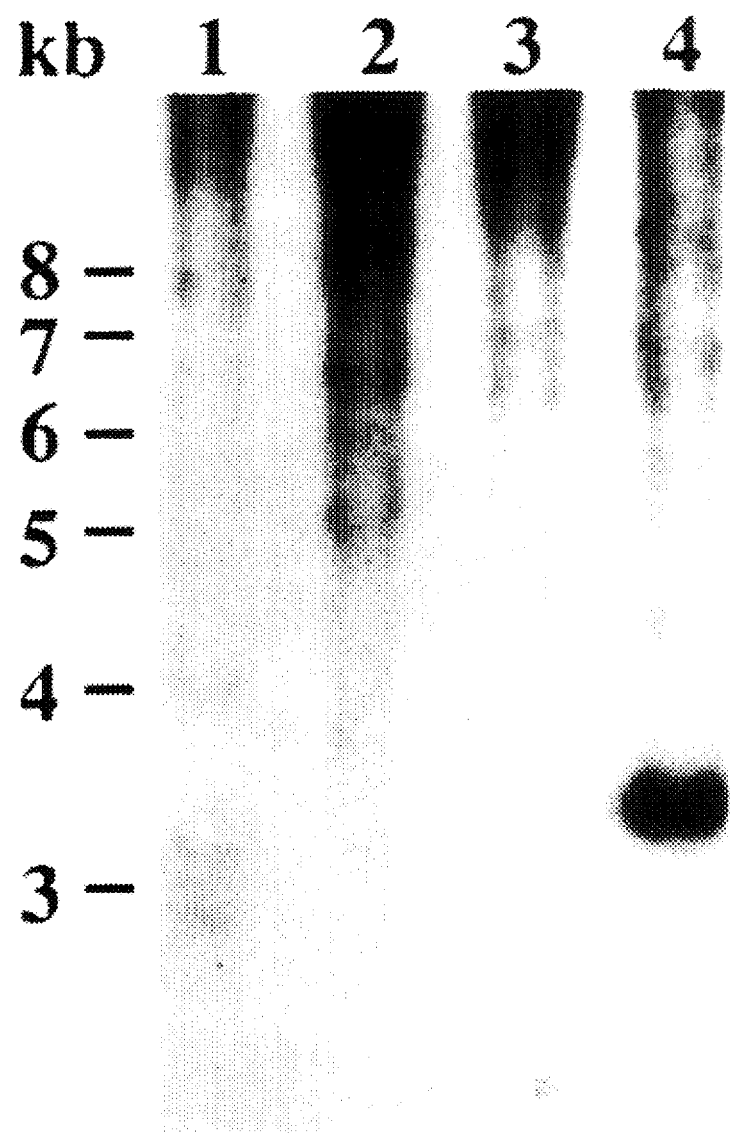
FIG. 3. Southern blot analysis of *P. haemolytica* strain NADC-D60 DNA digested with EcoRI lane 1, ClaI lane 2, PstI lane 3, or HindIII lane 4. The membrane was hybridized with an *E. coli* aroA probe and washing was performed under low-stringency conditions.

For methylation, the hybrid plasmid was electroporated into *E. coli* strain DH10B with or without a cosmid containing cloned PhaI methyltransferase gene. Plasmid DNA was isolated and purified by CsCl gradient centrifugation. PhaI methyltransferase-treated hybrid plasmid was electroporated into *P. haemolytica* strain NADC-D60 and then was reisolated by the above procedures. Plasmid DNA was reisolated from an ampicillin-resistant *P. haemolytica* transformant by the above procedures. The isolated plasmid DNA was tested for resistance to PhaI digestion as shown in FIG. 2.

Example 4

This example demonstrates that methylated DNA, but not unmethylated DNA, is able to transform *P. haemolytica*.

*Pasteurella haemolytica* strain NADC-D60 was grown in 250 ml Columbia broth (Difco) 3 hours at 37° C. with shaking to late logarithmic phase. The bacteria were centrifuged at 5000 G 15 minutes and the pellet resuspended in 272 mM sucrose at 0° C. The bacteria were washed 4 times in 272 mM sucrose with 5 minute centrifugation at 16,000 G and finally suspended at 50:50 vol:vol packed bacteria:272 mM sucrose on ice. Competent bacteria (100 μl) were mixed with 1 μg hybrid plasmid DNA (harvested from three sources: *E. coli* DH10B with methyltransferase (PhaIMtase); *E. coli* DH10B without methyltransferase; *P. haemolytica* NADC-D60) in 3 separate 1 mm electroporation cuvettes (Bio-Rad), plus a fourth no-DNA control. The cells were quickly electroporated after addition of DNA (Bio-Rad Gene pulser) at 1500 V, 800 ohm, 25 uFd with resultant time constants ranging from 7.8 to 8.9 msec. Columbia broth (1 ml, 0° C.) was immediately added to the electroporated cells and the suspension was kept on ice approximately 10 minutes. The electroporated cells were allowed to recover at 37° C. with gentle shaking for 1 hour, then broth containing 20 μg/ml ampicillin was added to bring the final ampicillin concentration to 10 μg/ml and the cells were incubated an additional hour at 37° C. with shaking. Ten-fold dilutions were plated in duplicate onto blood agar plates containing 5% bovine blood and 10 μg/ml ampicillin. Undiluted cells electroporated with hybrid plasmid obtained from *E. coli* containing PhaI methyltransferase were plated on 2 μg/ml chloramphenicol after the first hour of recovery. Colonies were enumerated after overnight incubation at 37° C. and representative colonies were checked for plasmid content.

Hybrid plasmid (pPhΔaroACm$^R$pD80) passed through *E. coli* containing PhaI methyltransferase in a cosmid was able to transform *P. haemolytica* serotype 1. The hybrid plasmid was stably maintained through multiple passages under selective pressure. Whereas DNA not exposed to PhaI methyltransferase was unable to transform *P. haemolytica*, DNA methylated by PhaI methyltransferase in *E. coli* yielded $10^3$ transformants per/μg plasmid (Table 1). Plasmid DNA passed through *P. haemolytica* yielded $10^5$ transformants per/μg plasmid. This experiment demonstrates that the restriction-modification system of PhaI is important for introduction of exogenous DNA into *P. haemolytica* serotype 1.

The plating efficiency of transformants was 2 logs lower on chloramphenicol than on ampicillin. All transformants recovered, however, were resistant to both ampicillin, and chloramphenicol upon passage.

The possibility that a system similar to *E. coli* mcr, mrr, is active in *P. haemolytica* was investigated by passage of pPhΔroACm$^R$pD80 through *E. coli* strain GM2163 previously transformed with the recombinant cosmid containing PhaI methyltransferase (Raleigh et at., *Proc. Natl. Acad. Sci.* 83:9070–9074 (1986)). Since strain GM2163 is dam-, the resultant DNA would only be modified at PhaI sites (Marinus et al., *Mol. Gen. Genet.* 192:288–289 (1983)). Efficiency of transformation with this DNA, however, was not substantially different than that using DNA obtained from PhaI Mtase which is dam-methylated (Table 1). It is possible a second restriction system, not readily detectable in cell extracts, is active in *P. haemolytica* A 1. Genes have been described in *Neisseria gonnorhea* MS11 which encode for restriction enzymes which are expressed at levels too low to detect biochemically (Stein et at., *J. Bact.* 74:4899–4906 (1992).

TABLE 1

Transformation efficiency of *P. haemolytica* NADC-D60 with hybrid plasmid pPhΔaroACm$^r$pD80 purified from various sources$^a$.

| Source of DNA$^b$ | Amp$^R$ transformants$^c$ CFU/μg DNA | CM$^R$ transformants$^d$ CFU/μg DNA |
|---|---|---|
| E. coli DH10B | 0 | nd$^e$ |
| E. coli PhaIMtase | 1 × 10$^3$ | 5 |
| E. coli GM2163 | 5 × 10$^2$ | nd |
| P. haemolytica NADC-D60 | 1 × 10$^5$ | nd |

$^a$One μg DNA introduced by electroporation using same competent preparation.
$^b$Purified by CsCl-EtBr gradient centrifugation.
$^c$Colonies on plates containing 10 μg/ml ampicillin, cells recovered 2 hours prior to plating.
$^d$Colonies on plates containing 2 μg/ml chloramphenicol, cells recovered 1 hours prior to plating.
$^e$Not done.

This experiment demonstrates that the restriction-modification system of PhaI plays an important role in the difficulties researchers have encountered in their attempts to introduce exogenous DNA into *P. haemolytica* serotype 1. Protection against PhaI activity may allow genetic manipulation of this organism, which could lead to dramatic improvements in our understanding of pathogenesis and control of pneumonic pasteurellosis in cattle.

Example 5

This example demonstrates the molecular cloning and sequencing of *P. haemolytica* aroA.

Cloning or *P. haemolytica* aroA. Restriction fragments of *P. haemolytica* genomic DNA were fractionated by agarose gel electrophoresis. The fragments were probed for homology to a 1.3 kb *E. coli* aroA fragment by Southern analysis. Under conditions of low stringency, a 3.2-kb HindIII fragment of *P. haemolytica* genomic DNA hybridized with radiolabeled *E. coli* aroA (FIG. 3). The HindIII fragment was isolated from an agarose gel by electroelution and it was cloned into HindIII digested pSK. The recombinant plasmid, pPharoA1, bearing *P. haemolytica* aroA was identified by complementation of *E. coli* aroA mutant AB2829 on M9 minimal media containing ampicillin. A Cla I, HindIII double digest of pPharoA1 generated a 2.2-kb fragment which was cloned into the AccI and HindIII sites of pSK- giving rise to pPharoA2. Plasmid pPharoA2 also complemented growth of *E. coli* AB2829 on M9 minimal media. This plasmid was used to determine the sequence of *P. haemolytica* aroA.

Southern Blotting and Molecular Cloning of *P. haemolytica* aroA Methods. *P. haemolytica* genomic DNA was prepared by the method for isolating DNA from gram-negative bacteria. Southern blotting of *P. haemolytica* restriction fragments fractionated by electrophoresis on a 0.75% agarose was performed as described previously. Blots were hybridized with a radioactively labeled 1.3-kb *E. coli* aroA fragment. The aroA probe was amplified (Gene-AMP by Perkin Elmer Inc., Branchburg, N.J.) from *E. coli* X-L1 Blue (Stratagene, Inc. S.D. Calif.) genomic DNA using PCR. The primers: 5'-TTCATGGAATCCCTTGACGTTACAACCCATC-3' and 5'-AGGCTGCCTGGCTAATCCGCGCCAG-3' used in the PCR reaction hybridize with *E. coli* aroA nucleotides −3 through 28 and 1308 through 1323 respectively. The primers were synthesized using an Applied Biosystems oligonucleotide synthesizer (Applied Biosystems Inc.) by the Nucleic Acids Facility, Iowa State University (Ames, Iowa). DNA was radiolabeled with [α-$^{32}$P] dCTP using a random priming kit (Boehringer Mannheim Biochemicals, Indianapolis, Ind.). Nylon membranes (Hybond-N, Amersham Corp., Arlington Heights, Ill.) were incubated with hybridization solution 5×SSC (1×SSC is 0.15M NaCl and 0.015M sodium citrate), 5×Denhardts solution (Maniatis, *Molecular Cloning*, Cold Spring Harbor Laboratory, Cold Spring Harbor, N.Y. (1982)), 0.1% SDS, 10 μg/ml sonicated salmon sperm DNA, containing $1\times10^7$ CPM of $^{32}$P-labeled probe and 50% formamide at 42° C. After hybridization for 18 hours, membranes were washed twice with 1×SSC and 0.1% SDS for 10 minutes at RT and two times with 1×SSC and 0.1% SDS buffer at 42° C. for 15 minutes. Membranes were exposed to X-AR (Eastman Kodak Co., Rochester, N.Y.) at −80° C. for 24 hours. A positive signal corresponding to a 3.2-kb HindIII fragment of *P. haemolytica* chromosomal DNA was identified.

HindIII digested *P. haemolytica* DNA fragments ranging from 3.0–3.4 kb in length were electroeluted from a 1% agarose gel. The HindIII genomic fragments were added to HindIII digested alkaline phosphatase treated pSK-vector (Stratagene, Inc. S.D. Calif.) and ligated overnight at 10° C. with T4 ligase (BRL, Gaithersburg, Md.). The ligation mix was diluted 1:10 with distilled water and electroporated using a Gene Pulser (Bio-Rad Laboratories, Richmond, Calif.) into *E. coli* aroA mutant AB2829 (Pittard et al., *J. Bact.* 91:1494–1508 (1966)). A recombinant plasmid, pPharoA1, complemented AB2829 grown on M9 minimal media containing phosphate buffer, 1 mM $MgSO_4$, 0.1 mM $CaCl_2$, 0.2% glucose, thiamine 10 μg/ml, 1.5% Noble agar (Difco) and 50 μg/ml ampicillin (Ausubel et al., supra). A ClaI, HindIII double digest of pPharoA1 produced a 2.2 kb fragment which when cloned into the AccI, HindIII sites of pSK- gave rise to pPharoA2. The recombinant plasmid, pPharoA2, which also complemented growth of AB2829 on minimal plates, was used to sequence *P. haemolytica* aroA.

Nucleotide sequence of *P. haemolytic* aroA. The nucleotide sequence and the deduced amino acid sequence of *P. haemolytica* aroA are shown in FIG. 4 and SEQ ID NOS: 1 and 2. An open reading frame of 1302 bases with a coding capacity of 434 amino acid residues was discerned. The deduced molecular weight is 47,296 and the G+C content of the aroA coding region is 43%. The predicted amino acid sequence of *P. haemolytica* aroA showed 75, 70, 69, and 68% identity with *Pasteurella multocida*, *Klebsiella pneumoniae*, *Yersenia entercolitica*, and *Escherichia coli*, respectively.

*P. haemolytica* aroA, like *P. multocida* aroA (Homchampa et al. *Molec. Microbiol.* 23:3585–3593 (1992)), appears to be transcribed from its own promoter. This differs from the usual genetic arrangement in gram-negative bacteria where aroA and serC constitute an operon with aroA distal to the promoter. Evidence to support this claim are the findings that: (1) the nucleotide sequence upstream of aroA on clone pPharoA2 shows no homology with serC genes and (2) complementation of *E. coli* AB2829 by *P. haemolytica* aroA contained on the 2.2 kb fragment is independent of the fragment's orientation on the cloning vector.

DNA sequencing and Analysis. DNA sequencing was done by the dideoxy nucleotide termination method with single or double stranded templates using the Sequanase 2.0 kit (United States Biochemicals, Cleveland, Ohio). A series of ordered deletions were made in *P. haemolytica* aroA contained on pPharoA2 using an Erase-a-base kit (Promega Corp. Madison, Wis.). Gaps in the sequence were completed using DNA primers synthesized by the DNA core facility at Iowa State University (Ames, Iowa). DNA sequence analysis was done with MacDNASIS Pro (Hitachi Software Ltd., San Bruno, Calif.) and MacVector (Kodak Co., New Haven, Conn.) software.

Example 6

This example demonstrates the construction of a defined *P. haemolytica* aroA mutant.

Construction of a *P. haemolytica* aroA mutant. The deletion plasmid, pPhΔaroACm$^R$ (Table 2), was constructed from pPharoA2 as described above and amplified in *E. coli* containing a cosmid clone carrying the PhaI methyltransferase gene on a 20-kb *P. haemolytica* DNA fragment. Although resistant to PhaI endonuclease digestion, introduction of pPhΔaroACm$^R$ into *P. haemolytica* strain NADC-D60 by electroporation failed to generate Cm resistant colonies. The inability to transform *P. haemolytica* with pPhΔaroACm$^R$ suggested that plasmids containing a ColE1 origin do not replicate in this bacterium.

TABLE 2

| Bacterial strains and plasmids used | | |
|---|---|---|
| Strains | Characteristics | Source/Reference |
| *E. coli* | | |
| AB2829 | K-12 strain with mutation in aroA | Pittard and Wallace (1966) |
| DH10B | Cloning strain used in this work | BRL |
| XL 1-Blue | Strain used for DNA sequencing | Stratagene |
| *P. haemolytica* | | |
| NADC-D60 | Serotype 1 plasmidless | NADC/R. Briggs |
| NADC-D70 | Serotype 1 containing pD70 | NADC/R. Briggs |
| NADC-D80 | Serotype 1 containing pD80 | NADC/R. Briggs |
| Plasmids | | |
| pSK | cloning vector (Amp$^R$) | Stratagene |
| pBCSK | cloning vector (Cm$^R$) | Stratagene |
| pD70 | 4.2 kb plasmid encoding streptomycin$^R$ | NADC/R. Briggs |

TABLE 2-continued

| Bacterial strains and plasmids used | | |
|---|---|---|
| Strains | Characteristics | Source/Reference |
| pD80 | 4.2 kb plasmid encoding Amp$^R$ | NADC/R. Briggs |
| pPharoA1 | 3.2 kb HindIII fragment containing *P. haemolytica* aroA (pSK) | This work |
| pPharoA2 | HindIII ClaI digest of pPharoA1 resulted in 2.2 kb aroA fragment (pSK) | This work |
| pPharoA3 | same insert as pPharoA2 on pBCSK | This work |
| pPhΔaroACm$^R$ | StyI NdeI digest of pPharoA2 Cm$^R$ fragment inserted into deletion site | This work |
| pPhΔaroACm$^R$pD80 | SmaI digested pPhΔaroACm$^R$ joined to ScaI digested pD80 | This work |
| pPhAmp$^R$ | 2.2 kb Sau 3A fragment of pD80 cloned into pBCSK | This work |
| pPharoA$^-$Amp$^R$ | Amp$^R$ fragment of pD80 inserted into unique NdeI site of pPharoA3 | This work |
| pPharoA$^-$Amp$^R$pD70 | HindIII digested pPharoA$^-$Amp$^R$ joined to HindIII digested pD70 | This work |

Since we have shown that the PhaI methylated hybrid plasmid consisting of plasmids pPhΔaroACm$^R$ joined with *P. haemolytica* pD80 (Amp$^R$) could be used to transform *P. haemolytica* strain NADC-D60 (see above), we investigated the possibility that aroA mutants might arise after transformation with the hybrid plasmid by recombination with the genomic copy of the aroA gene, i.e., "replacement" of the gene. *P. haemolytica* harboring the hybrid plasmid pPhΔaroACm$^R$pD 80 were passed for >100 generations in Columbia broth without antibiotics and plated onto blood-agar plates. The colonies were then replica plated onto blood-agar plates containing 5 μg/ml ampicillin. All colonies had an Amp$^R$ phenotype, suggesting that the plasmid was stable in *P. haemolytica*. This was confirmed by Southern blot analysis which showed that intact plasmid was present in all the Amp$^R$ colonies that were analyzed.

Because the number of *P. haemolytica* transformants generated with hybrid plasmid pPhΔaroACm$^R$pD80 (Amp$^R$Cm$^R$) was 100-fold greater with plasmid isolated from *P. haemolytica* ($10^5$ CFU/μg DNA) than from *E. coli* containing the PhaI methyltransferase gene (see above), we reasoned that a replacement plasmid isolated from *P. haemolytica* would be resistant to enzymatic digestion upon reintroduction into *P. haemolytica*, and thus more likely to give rise to mutants via homologous recombination. The improved efficiency is presumed to be the result of DNA modifications in *P. haemolytica* in addition to that of PhaI methylation. With this in mind, hybrid plasmid pPhΔaroACm$^R$pD80 was isolated from *P. haemolytica* strain NADC-D60 and CsCl purified by the methods described previously. The hybrid plasmid was digested with HindIII and XbaI to produce two fragments consisting of pD80 and pPhΔaroACm$^R$. Linear deletion plasmid, pPhΔaroACm$^R$, was isolated by electroelution and purified using "Glass-Max" beads (BRL, Gaithersburg, Md.). Approximately 5 μg of the linear plasmid was electroporated into *P. haemolytica* NADC-D60. The cells were recovered in 1 ml Columbia broth and shaken at 37° C. for 1 hour prior to plating on Blood-agar plates containing 10 μg/ml chloramphenicol. No Cm$^R$ colonies were detected after incubation at 37° C. for 48 hours. However, this result was not totally unexpected since there have been few reports of the successful establishment of linear DNA into bacteria.

Five μg of linearized pPhΔaroACm$^R$, isolated from *P. haemolytica*, was treated with Klenow and deoxynucleoside triphosphates to produce blunt ends. The DNA was then ligated with T4 ligase overnight to form a circular replacement plasmid. The plasmid was phenol chloroform extracted, ethanol precipitated, resuspended in distilled water, and reintroduced into *P. haemolytica* by electroporation. The cells were transferred to Columbia broth and allowed to recover for 1 hour. The cells were spread on blood-agar plates containing antibiotic and incubated at 37° C. for 48 hours. This experiment also failed to generate Cm$^R$ *P. haemolytica* colonies.

Additional efforts to produce an aroA mutant resulted in construction of a new replacement plasmid in which aroA was insertionally inactivated by the *P. haemolytica* β-lactamase gene. This antibiotic resistance cassette was chosen to select gene replacement candidates because we had found that survival of *P. haemolytica* transformed with pPhΔaroACm$^R$pD80 was approximately 100-fold greater ($10^3$ CFU/μgDNA) on blood-agar plates containing ampicillin than on blood-agar plates containing chloramphenicol.

Molecular cloning of *P. haemolytica* β-lactamase gene was done as follows. Purified pD80 was partially digested with Sau3A, phenol-chloroform extracted, and ethanol precipitated. The fragments were resuspended in T.E. and ligated overnight into BamHI-digested pBCSK (Stratagene Inc., La Jolla, Calif.). The ligated mixture was diluted 1:10 with water and electroporated into *E. coli* DH10B. The cells were recovered in 1 ml SOC for 1 hour and spread on LB-plates containing 50 μg/ml ampicillin and 20 μg/ml chloramphenicol. Restriction enzyme analysis on plasmid isolated from an ampicillin, chloramphenicol resistant *E. coli* clone revealed a 2.2 kb *P. haemolytica* insert in pBCSK. This plasmid was designated pPhAmp$^R$. To demonstrate that pPhAmp$^R$ did not possess the pD80 origin of replication, the plasmid was amplified in *E. coli* DH10B which also contained the PhaI methyltransferase clone. Plasmid pPhAmp$^R$ was isolated from *E. coli* as described previously, CsCl purified and introduced into *P. haemolytica* by electroporation. Since this plasmid did not confer ampicillin resistance to *P. haemolytica* strain NADC-D60, we concluded that the antibiotic resistant fragment did not contain the pD80 origin of replication and that the fragment encoding the β-lactamase gene could be used to construct a deletion plasmid.

Construction of the deletion plasmid involved the following. The β-lactamase gene was excised from pPhAmp$^R$ by HindIII, XbaI digestion and treated with Klenow and deoxyribonucleotides to generate blunt ends. The β-lactamase gene was ligated into the Klenow treated unique NdeI site of pPharoA3 (FIG. 5) to produce pPharoA$^-$Amp$^R$. Insertional inactivation of aroA on pPharoA$^-$amp$^R$ was demonstrated by failure of the plasmid to complement AB2829. Plasmid pPharoA$^-$Amp$^R$ was amplified in *E. coli* DH10B (BRL) which also contained the recombinant cosmid carrying PhaI methylase recombinant cosmid. Although PhaI methylated pPharoA$^-$Amp$^R$ was resistant to digestion by PhaI, introduction of this plasmid into *P. haemolytica* failed to generate ampicillin resistant colonies.

Figure 5:
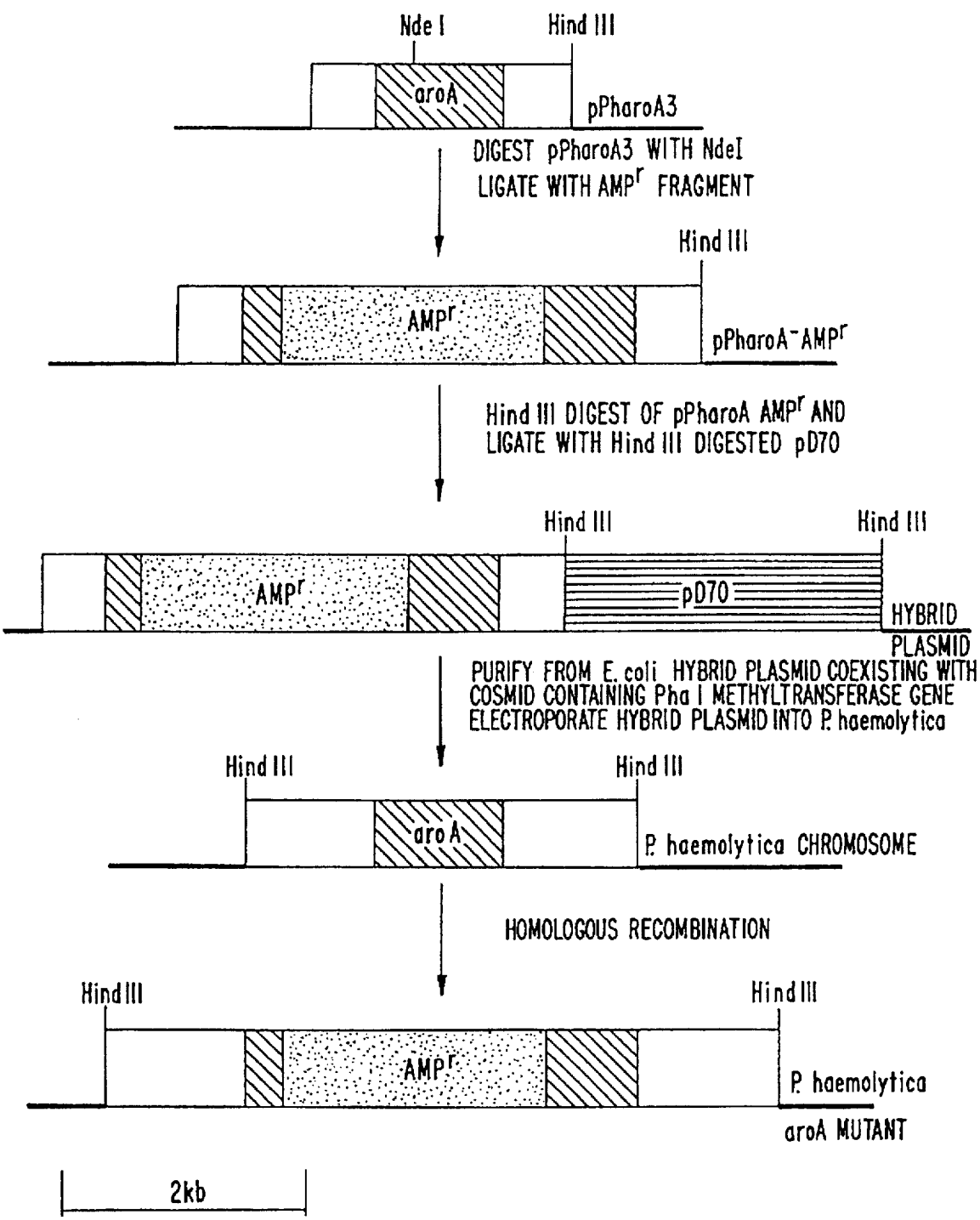
FIG. 5. Construction of a *P. haemolytica* aroA mutant. The hybrid plasmid pPharoA$^-$Amp$^R$pD70 was successfully used to produce an aroA mutant.
Figure 6A:
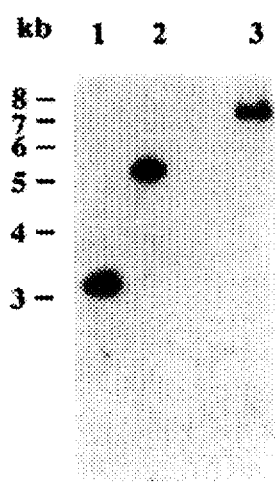
FIGS. 6A–6D. Southern hybridization of genomic DNAs from the parental strain, *P. haemolytica* strain NADC-D60, the aroA mutant, and *P. haemolytica* strain NADC-D70 and the hybrid plasmid pPharoA$^-$Amp$^R$pD70. All the DNAs used in the blots shown here were digested with HindIII.
Figure 6B:
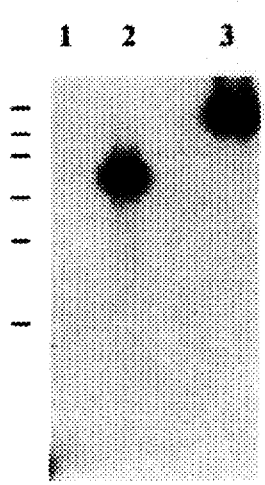
Figure 6C:
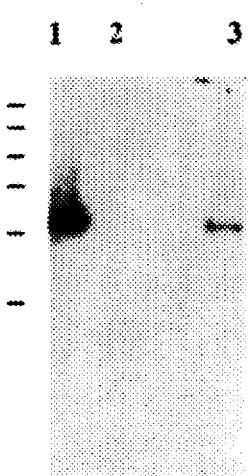
Figure 6D:
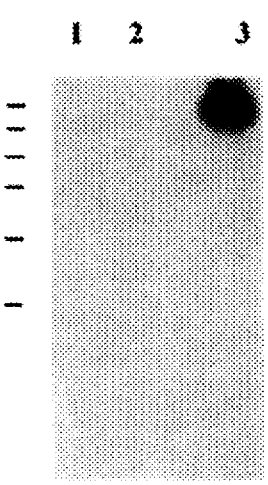

To increase the likelihood of allelic replacement between the deletion plasmid's inactivated aroA and *P. haemolytica* chromosome, we constructed an aroA$^-$ mutant-hybrid plasmid consisting of pPharoA$^-$Amp$^R$ and a 4.2-kb *P. haemolytica* plasmid (pD70, which confers streptomycin resistance (Sm$^R$)) (FIG. 5). The Sm$^R$ plasmid was isolated from *P. haemolytica* using methods described previously. The str$^R$ plasmid was digested at a unique HindIII site and ligated with HindIII digested pPharoA$^-$Amp$^R$. The resultant hybrid plasmid, pPharoA$^-$ Amp$^R$pD70 (FIG. 5), was PhaI methyltransferase modified in *E. coli* DH10B containing the cosmid clone of the PhaI methylase gene. The hybrid plasmid was isolated from *E. coli*, CsCl purified and introduced into *P. haemolytica* strain NADC-D60 by electroporation. The cells were resuspended in Columbia broth for 2 hours at 37° C. and spread on blood-agar plates containing 10 μg/ml ampicillin. Transformation efficiency of the hybrid plasmid yielded approximately $10^1$ ampicillin resistant colonies/μg DNA. Eight Amp$^R$ colonies were grown overnight in Columbia broth containing 1 μg/ml ampicillin. Chromosomal DNAs from the parental strain and from the Amp$^R$ colonies were digested with HindIII and probed by Southern blotting with *P. haemolytica* aroA, pBCSK, and pD70. The results indicated that intact pPharoA$^-$Amp$^R$pD70 was present in the Amp$^R$ colonies.

Eight Amp$^R$ clones were grown overnight in Columbia broth containing 1 μg/ml ampicillin. Chromosomal DNAs from the parental strain and from the Amp$^R$ clones were digested with HindIII and analyzed by Southern blotting with *P. haemolytica* aroA, pBCSK, and pD70 radio-labeled probes. The results indicated that intact pPharoA$^-$Amp$^R$pD70 was present in the Amp$^R$ clones (data not shown). The eight Amp$^R$ cultures were transferred to Columbia broth containing 1 μg/ml ampicillin and cultured at 37° C. The bacteria were transferred to fresh media daily and this process was continued for approximately 100 generations. The eight cultures were streaked for isolation without antibiotic selection and a single colony of each was passed into Columbia broth containing either 1 μg/ml ampicillin or 1 μg/ml chloramphenicol. Two of the eight survived on the broth containing ampicillin, none on chloramphenicol. Passage from ampicillin broth onto blood-agar plates containing either ampicillin or chloramphenicol or streptomycin confirmed the two clones were Amp$^R$, Cm$^S$, Sm$^S$. Also the two Amp$^R$ clones were spread onto plates of chemically-defined medium for *P. haemolytica* cultivation (Wessman, *Applied Microbiol.* 14:597–602 (1966)). This medium lacks the aromatic amino acid tryptophan. The parent strain grew on the defined medium but the Amp$^R$ clones did not. Upon addition of tryptophan to the defined medium, growth of the Amp$^R$ clones was comparable to that of the parent strain. The *E. coli* aroA mutant AB2829 also required tryptophan to grow on the chemically-defined medium for *P. haemolytica* cultivation. DNAs from the two colonies possessing Amp$^R$, Cm$^S$, Sm$^S$, aroA$^-$ phenotypes were analyzed by Southern blotting. The results indicated that both had insertionally inactivated aroAs. Moreover, Southern blotting also confirmed that both pD70 and pBCSK sequences were no longer present in the aroA mutants (FIG. 6).

Construction methods for *P. haemolytica* mutants. The 4.2 kb ampicillin resistance encoding plasmid of *P. haemolytica* (pD80) was partially digested with Sau3A and ligated into the BamHI site of pBCSK$^+$ (Cm$^R$) (Stratagene Inc., La Jolla, Calif.). The ligation mix was diluted 1:10 in distilled water and electroporated into *E. coli* DH-10B (BRL, Gaithersburg, Md.). After recovery in 1 ml SOC at 37° C., the cells were spread onto B-agar plates containing 50 μg/ml ampicillin. Plasmid, pPhAmp$^R$, contained a 2.2-kb *P. haemolytica* fragment which imparted ampicillin resistance to *E. coli* to up to 100 μg/ml. Plasmid, pPhAmp$^R$, was digested with HindIII and XbaI digestion and the fragment ends were made blunt by incubation with deoxynucleotide triphosphates and the large Klenow fragment of E. coli polymerase I. The fragment encoding ampicillin resistance was electroeluted. P. haemolytica aroA contained on pPharoA3 was digested at an unique restriction site within the coding region of aroA with NdeI and the fragment ends were made bunt as described previously. The fragment encoding ampicillin resistance was blunt-end ligated with T4 ligase into pPharo2 thus generating pPharoA⁻Amp$^R$. Plasmid pPharoA⁻Amp$^R$ was digested with HindIII and dephosphorylated with calf alkaline phosphatase. A 4.2 kb plasmid encoding Sm$^R$ isolated from P. haemolytica strain NADC-D70 (Chang et al., J. DNA Sequencing and Mapping 3:89–97 (1992)) was also digested with HindIII and the two plasmids were ligated with T4 ligase to generate the hybrid plasmid pPharoA⁻Amp$^R$pD70. The hybrid plasmid was electroporated into E. coil Pha IMtase which contained the PhaI methyltransferase gene on cosmid pLAFRX (Ausubel, supra).

P. haemolytica strain NADC-D60 is a plasmidless strain which was isolated from a cow with pneumonic pasteurellosis. The PhaI methylated hybrid plasmid was CsCl purified and 1 μg plasmid and 30 μl of P. haemolytica strain NADC-D60 were transferred to an 0.2 cm. cuvette and electroporated at 15,000 volts/cm with 800 ohms. The resultant time constant was approximately 9 milliseconds. Cells were transferred to 2 ml Bacto Columbia broth (Difco Labs, Detroit, Mich.) and incubated at 37° C. for two hours and spread on Difco Columbia blood-agar plates containing 10 μg/ml ampicillin. Eight ampicillin resistant P. haemolytica colonies were isolated after incubation at 37° C. for 18 hours. The colonies were then transferred to Bacto-Columbia broth containing 1 μg/ml ampicillin and incubated at 37° C. Daily passage into fresh medium containing 1 μg/ml ampicillin was carried out for three days at which time the cultures were transferred onto Columbia broth blood-agar plates containing 10 μg/ml ampicillin and incubated at 37° C. overnight. The next day, colonies were replica-plated onto Columbia broth blood-agar plates containing 10 μg/ml or 50 μg/ml streptomycin and a chemically-defined medium for P. haemolytica cultivation (Wessman, supra). The defined medium contains 15 amino acids and includes the aromatic amino acids phenylalanine and tyrosine but not tryptophan. The clones unable to grow on the chemically-defined medium for P. haemolytica cultivation were presumed to be aroA⁻. Genomic DNA isolated from colonies with Amp$^R$, Cm$^S$, Sm$^S$, aroA-phenotypes were analyzed by Southern blotting. Southern blotting was performed as described previously with the exception that after hybridization the membranes were washed twice for 10 minutes each in 1×SSC and 0.1% SDS at 42° C. and twice more for 15 minutes each in 0.1×SSC and 0.1% SDS at 65° C.

We claim:

1. A chimeric plasmid for unstable introduction of genetic material into *P. haemolytica* comprising two plasmids covalently linked to each other, wherein the first plasmid is a 4.2 kb $Str^R$ plasmid of *P. haemolytica* deposited at the American Type Culture Collection as Accession No. ATCC 69499; and the second plasmid is a plasmid which cannot replicate in *P. haemolytica*.

2. The chimeric plasmid of claim 1 further comprising:

a region of the chromosome of *P. haemolytica* wherein said region harbors a mutation.

3. The chimeric plasmid of claim 1 further comprising:

a gene of the chromosome of *P. haemolytica* wherein said gene harbors a mutation.

4. The chimeric plasmid of claim 1 further comprising:

a DNA segment made by the process of:

isolating a DNA segment from *P. haemolytica* and subjecting the segment to mutagenesis.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Escherichia coli ( x i ) SEQUENCE DESCRIPTION: SEQ ID NO:1:

AGGCTGCCTG GCTAATCCGC GCCAG       25

( 2 ) INFORMATION FOR SEQ ID NO:2:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Escherichia coli ( x i ) SEQUENCE DESCRIPTION: SEQ ID NO:2:

TTCATGGAAT CCCTTGACGT TACAACCCAT C                                          31

( 2 ) INFORMATION FOR SEQ ID NO:3:

( i ) SEQUENCE CHARACTERISTICS:
        ( A ) LENGTH: 1556 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pasteurella haemolytica ( i x ) FEATURE:
        ( A ) NAME/KEY: CDS
        ( B ) LOCATION: 184..1486

( x i ) SEQUENCE DESCRIPTION: SEQ ID NO:3:

```
TATGAGGCAT TACTGCGTGA AGGCGTGATT GTTCGCTCGA TAGCAGGTTA TGGAATGCCG          60

AATCATTTAC GCATTAGTAT GCCTTTACCG CAAGAAAACG AGAGATTTTT TACTGCCTTA         120

TTGAAAGTGT TAGCTTAACA AGCGGTTACC TTTTATGAAA ATTTTACAAA TTAAAGAGA          180

AAA ATG GAA AAA CTA ACT TTA ACC CCG ATT TCC CGA GTA GAA GGC GAG          228
    Met Glu Lys Leu Thr Leu Thr Pro Ile Ser Arg Val Glu Gly Glu
    1               5                   10                  15

ATC AAT TTA CCT GGT TCT AAA AGC CTG TCT AAC CGA GCC TTA TTA TTA          276
Ile Asn Leu Pro Gly Ser Lys Ser Leu Ser Asn Arg Ala Leu Leu Leu
                20                  25                  30

GCC GCC TTA GCC ACC GGT ACG ACT CAA GTG ACC AAT TTA TTA GAT AGT          324
Ala Ala Leu Ala Thr Gly Thr Thr Gln Val Thr Asn Leu Leu Asp Ser
            35                  40                  45

GAT GAT ATT CGA CAT ATG CTC AAT GCC TTA AAA GCG TTA GGC GTG AAA          372
Asp Asp Ile Arg His Met Leu Asn Ala Leu Lys Ala Leu Gly Val Lys
        50                  55                  60

TAT GAG CTA TCG GAC GAT AAA ACC GTC TGT GTA CTT GAA GGG ATT GGT          420
Tyr Glu Leu Ser Asp Asp Lys Thr Val Cys Val Leu Glu Gly Ile Gly
    65                  70                  75

GGA GCT TTT AAG GTT CAA AAC GGC TTA TCA CTG TTT CTC GGC AAT GCA          468
Gly Ala Phe Lys Val Gln Asn Gly Leu Ser Leu Phe Leu Gly Asn Ala
80                  85                  90                  95

GGC ACG GCA ATG CGA CCA CTT GCA GCA GCA TTG TGT TTA AAA GGT GAG          516
Gly Thr Ala Met Arg Pro Leu Ala Ala Ala Leu Cys Leu Lys Gly Glu
                100                 105                 110

GAA AAA TCC CAA ATC ATT CTT ACC GGT GAA CCA AGA ATG AAA GAA CGC          564
Glu Lys Ser Gln Ile Ile Leu Thr Gly Glu Pro Arg Met Lys Glu Arg
            115                 120                 125

CCG ATT AAA CAC TTA GTC GAT GCT TTA CGC CAA GTA GGG GCA GAG GTA          612
Pro Ile Lys His Leu Val Asp Ala Leu Arg Gln Val Gly Ala Glu Val
        130                 135                 140

CAG TAT TTA GAA AAT GAA GGC TAT CCA CCG TTG GCA ATT AGC AAT AGC          660
Gln Tyr Leu Glu Asn Glu Gly Tyr Pro Pro Leu Ala Ile Ser Asn Ser
    145                 150                 155

GTT TGC AGG GGC GGA AAA GTG CAA ATT GAC GGC TCG ATT TCC AGC CAA          708
Val Cys Arg Gly Gly Lys Val Gln Ile Asp Gly Ser Ile Ser Ser Gln
160                 165                 170                 175

TTT CTA ACC GCA TTG CTG ATG TCT GCC CCA TTA GCG GAA GGC GAT ATG          756
```

| | | | | | | | | | | | | | | | |
|---|---|---|---|---|---|---|---|---|---|---|---|---|---|---|---|
|Phe|Leu|Thr|Ala|Leu<br>180|Leu|Met|Ser|Ala|Pro<br>185|Leu|Ala|Glu|Gly|Asp|Met<br>190|

| | | | | | | | | | | | | | | | | |
|---|---|---|---|---|---|---|---|---|---|---|---|---|---|---|---|---|
|GAA|ATT|GAG|ATT|ATC|GGT|GAT|CTG|GTA|TCA|AAA|CCT|TAT|ATT|GAT|ATT| 804 |
|Glu|Ile|Glu<br>195|Ile|Ile|Gly|Asp|Leu|Val<br>200|Ser|Lys|Pro|Tyr|Ile<br>205|Asp|Ile| |
|ACC|CTT|TCG|ATG|ATG|AAC|GAT|TTT|GGT|ATT|ACG|GTT|GAA|AAT|CGA|GAT| 852 |
|Thr|Leu|Ser<br>210|Met|Met|Asn|Asp|Phe|Gly<br>215|Ile|Thr|Val|Glu|Asn<br>220|Arg|Asp| |
|TAC|AAA|ACC|TTT|TTA|GTT|AAA|GGT|AAA|CAA|GGC|TAT|GTT|GCT|CCA|CAA| 900 |
|Tyr|Lys<br>225|Thr|Phe|Leu|Val|Lys<br>230|Gly|Lys|Gln|Gly|Tyr<br>235|Val|Ala|Pro|Gln| |
|GGT|AAT|TAT|TTG|GTG|GAG|GGA|GAT|GCC|TCT|TCT|GCC|TCT|TAT|TTC|TTA| 948 |
|Gly|Asn|Tyr|Leu|Val<br>245|Glu|Gly|Asp|Ala|Ser<br>250|Ser|Ala|Ser|Tyr|Phe|Leu<br>255| |
|Ala<br>240| | | | | | | | | | | | | | | | |
|GCC|TCC|GGT|GCG|ATT|AAG|GCA|GGT|AAA|GTA|ACG|GGC|ATT|GGT|AAA|AAA| 996 |
|Ala|Ser|Gly|Ala|Ile<br>260|Lys|Ala|Gly|Lys|Val<br>265|Thr|Gly|Ile|Gly|Lys<br>270|Lys| |
|TCG|ATC|CAA|GGC|GAC|CGC|TTG|TTT|GCC|GAT|GTG|TTG|GAA|AAA|ATG|GGG| 1044 |
|Ser|Ile|Gln|Gly|Asp<br>275|Arg|Leu|Phe|Ala|Asp<br>280|Val|Leu|Glu|Lys|Met<br>285|Gly| |
|GCA|AAA|ATC|ACT|TGG|GGA|GAG|GAT|TTT|ATT|CAA|GCC|GAG|CAA|TCC|CCG| 1092 |
|Ala|Lys|Ile|Thr<br>290|Trp|Gly|Glu|Asp|Phe<br>295|Ile|Gln|Ala|Glu|Gln<br>300|Ser|Pro| |
|CTA|AAA|GGC|GTA|GAT|ATG|GAT|ATG|AAT|CAT|ATT|CCT|GAT|GCG|GCA|ATG| 1140 |
|Leu|Lys<br>305|Gly|Val|Asp|Met|Asp<br>310|Met|Asn|His|Ile|Pro<br>315|Asp|Ala|Ala|Met| |
|ACG|ATT|GCA|ACA|ACC|GCT|TTA|TTT|GCC|GAA|GGA|GAA|ACA|GTT|ATC|CGC| 1188 |
|Thr|Ile|Ala|Thr|Thr<br>325|Ala|Leu|Phe|Ala|Glu<br>330|Gly|Glu|Thr|Val|Ile|Arg<br>335| |
|320| | | | | | | | | | | | | | | | |
|AAT|ATT|TAT|AAC|TGG|CGG|GTA|AAA|GAA|ACC|GAC|CGC|TTG|ACA|GCA|ATG| 1236 |
|Asn|Ile|Tyr|Asn|Trp<br>340|Arg|Val|Lys|Glu|Thr<br>345|Asp|Arg|Leu|Thr|Ala<br>350|Met| |
|GCA|ACC|GAA|TTG|CGT|AAA|GTC|GGG|GCA|GAG|GTA|GAA|GAA|GGG|GAA|GAA| 1284 |
|Ala|Thr|Glu|Leu|Arg<br>355|Lys|Val|Gly|Ala|Glu<br>360|Val|Glu|Glu|Gly|Glu<br>365|Glu| |
|GGG|GAA|GAT|TTT|ATT|CGG|ATT|CAA|CCG|CTT|GCG|TTA|GAA|AAC|TTC|CAG| 1332 |
|Gly|Glu|Asp|Phe<br>370|Ile|Arg|Ile|Gln|Pro<br>375|Leu|Ala|Leu|Glu|Asn<br>380|Phe|Gln| |
|CAC|GCT|GAA|ATT|GAA|ACC|TAT|AAC|GAT|CAC|CGT|ATG|GCA|ATG|TGT|TTT| 1380 |
|His|Ala|Glu<br>385|Ile|Glu|Thr|Tyr|Asn<br>390|Asp|His|Arg|Met|Ala<br>395|Met|Cys|Phe| |
|TCA|TTA|ATT|GCG|TTA|TCG|AAT|ACA|GAA|GTG|ACG|ATC|TTA|GAT|CCA|AAT| 1428 |
|Ser|Leu|Ile|Ala|Leu<br>405|Ser|Asn|Thr|Glu|Val<br>410|Thr|Ile|Leu|Asp|Pro|Asn<br>415| |
|400| | | | | | | | | | | | | | | | |
|TGT|ACC|GCT|AAA|ACG|TTC|CCG|ACT|TAC|TTT|AGG|GAC|TTG|GAA|AAA|TTA| 1476 |
|Cys|Thr|Ala|Lys|Thr<br>420|Phe|Pro|Thr|Tyr|Phe<br>425|Arg|Asp|Leu|Glu|Lys<br>430|Leu| |

| | | | | | | | | |
|---|---|---|---|---|---|---|---|---|
|TCG|GTC|AGA|T|AAAAGTAAAA|AAGGATTCAG|AAAACTGAAT|CCTTTTACG| 1526 |
|Ser|Val|Arg| | | | | | |

TTTTATTGTG GCAGACTAAG CCCAACCGCT      1556

( 2 ) INFORMATION FOR SEQ ID NO:4:

( i ) SEQUENCE CHARACTERISTICS:
        ( A ) LENGTH: 434 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

-continued

| | | | | | | | | | | | | | | |
|---|---|---|---|---|---|---|---|---|---|---|---|---|---|---|
| Met 1 | Glu | Lys | Leu | Thr 5 | Leu | Thr | Pro | Ile | Ser 10 | Arg | Val | Gly | Glu | Ile 15 |
| Asn | Leu | Pro | Gly 20 | Ser | Lys | Ser | Leu | Ser 25 | Asn | Arg | Ala | Leu 30 | Leu | Ala |
| Ala | Leu | Ala 35 | Thr | Gly | Thr | Thr | Gln 40 | Val | Thr | Asn | Leu | Leu 45 | Asp | Ser | Asp |
| Asp | Ile 50 | Arg | His | Met | Leu 55 | Asn | Ala | Leu | Lys | Ala 60 | Leu | Gly | Val | Lys | Tyr |
| Glu 65 | Leu | Ser | Asp | Asp 70 | Lys | Thr | Val | Cys | Val 75 | Leu | Glu | Gly | Ile | Gly 80 | Gly |
| Ala | Phe | Lys | Val | Gln 85 | Asn | Gly | Leu | Ser | Leu 90 | Phe | Leu | Gly | Asn | Ala 95 | Gly |
| Thr | Ala | Met | Arg 100 | Pro | Leu | Ala | Ala | Ala 105 | Leu | Cys | Leu | Lys | Gly 110 | Glu | Glu |
| Lys | Ser | Gln 115 | Ile | Ile | Leu | Thr | Gly 120 | Glu | Pro | Arg | Met | Lys 125 | Glu | Arg | Pro |
| Ile | Lys 130 | His | Leu | Val | Asp | Ala 135 | Leu | Arg | Gln | Val | Gly 140 | Ala | Glu | Val | Gln |
| Tyr 145 | Leu | Glu | Asn | Glu | Gly 150 | Tyr | Pro | Pro | Leu | Ala 155 | Ile | Ser | Asn | Ser | Val 160 |
| Cys | Arg | Gly | Gly | Lys 165 | Val | Gln | Ile | Asp | Gly 170 | Ser | Ile | Ser | Ser | Gln 175 | Phe |
| Leu | Thr | Ala | Leu 180 | Leu | Met | Ser | Ala | Pro 185 | Leu | Ala | Glu | Gly | Asp 190 | Met | Glu |
| Ile | Glu | Ile 195 | Ile | Gly | Asp | Leu | Val 200 | Ser | Lys | Pro | Tyr | Ile 205 | Asp | Ile | Thr |
| Leu | Ser 210 | Met | Met | Asn | Asp | Phe 215 | Gly | Ile | Thr | Val | Glu 220 | Asn | Arg | Asp | Tyr |
| Lys 225 | Thr | Phe | Leu | Val | Lys 230 | Gly | Lys | Gln | Gly | Tyr 235 | Val | Ala | Pro | Gln | Gly 240 |
| Asn | Tyr | Leu | Val | Glu 245 | Gly | Asp | Ala | Ser | Ser 250 | Ala | Ser | Tyr | Phe | Leu 255 | Ala |
| Ser | Gly | Ala | Ile | Lys 260 | Ala | Gly | Lys | Val | Thr 265 | Gly | Ile | Gly | Lys 270 | Lys | Ser |
| Ile | Gln | Gly 275 | Asp | Arg | Leu | Phe | Ala 280 | Asp | Val | Leu | Glu | Lys 285 | Met | Gly | Ala |
| Lys | Ile 290 | Thr | Trp | Gly | Glu | Asp 295 | Phe | Ile | Gln | Ala | Glu 300 | Gln | Ser | Pro | Leu |
| Lys 305 | Gly | Val | Asp | Met | Asp 310 | Met | Asn | His | Ile | Pro 315 | Asp | Ala | Ala | Met | Thr 320 |
| Ile | Ala | Thr | Thr | Ala 325 | Leu | Phe | Ala | Glu | Gly 330 | Glu | Thr | Val | Ile | Arg 335 | Asn |
| Ile | Tyr | Asn | Trp 340 | Arg | Val | Lys | Glu | Thr 345 | Asp | Arg | Leu | Thr | Ala 350 | Met | Ala |
| Thr | Glu | Leu | Arg 355 | Lys | Val | Gly | Ala | Glu 360 | Val | Glu | Glu | Gly 365 | Glu | Glu | Gly |
| Glu | Asp | Phe 370 | Ile | Arg | Ile | Gln 375 | Pro | Leu | Ala | Leu | Glu 380 | Asn | Phe | Gln | His |
| Ala 385 | Glu | Ile | Glu | Thr | Tyr 390 | Asn | Asp | His | Arg | Met 395 | Ala | Met | Cys | Phe | Ser 400 |
| Leu | Ile | Ala | Leu | Ser 405 | Asn | Thr | Glu | Val | Thr 410 | Ile | Leu | Asp | Pro | Asn 415 | Cys |

| | | | | | | | | | | | | | | |
|---|---|---|---|---|---|---|---|---|---|---|---|---|---|---|
| Thr | Ala | Lys | Thr | Phe | Pro | Thr | Tyr | Phe | Arg | Asp | Leu | Glu | Lys | Leu Ser |
| | | | 420 | | | | | 425 | | | | | 430 | |
| Val | Arg | | | | | | | | | | | | | |